United States Patent [19]

Andresen et al.

[11] 4,391,778

[45] Jul. 5, 1983

[54] METHOD AND APPARATUS FOR THE ANALYSIS OF MATERIALS BY CHROMATOGRAPHY AND MASS SPECTROMETRY

[75] Inventors: Brian D. Andresen; Kwokei J. Ng, both of Columbus, Ohio

[73] Assignee: The Ohio State University, Columbus, Ohio

[21] Appl. No.: 306,942

[22] Filed: Sep. 30, 1981

[51] Int. Cl.³ .................... G01N 31/08; H01J 27/00
[52] U.S. Cl. .................................. 422/89; 250/288; 250/423 R; 422/70; 436/149; 436/161
[58] Field of Search ............... 422/70, 89; 250/423, 250/288; 436/149, 161

[56] References Cited

U.S. PATENT DOCUMENTS

| | | | |
|---|---|---|---|
| 4,066,411 | 1/1978 | Fine et al. ............................. | 422/89 |
| 4,112,297 | 9/1978 | Miyagi et al. ........................ | 250/423 |

FOREIGN PATENT DOCUMENTS

| | | | |
|---|---|---|---|
| 55-94159 | 7/1980 | Japan .................................... | 422/89 |
| 708222 | 1/1980 | U.S.S.R. ............................... | 422/89 |

OTHER PUBLICATIONS

J. of Chrom., 112, (1975), 343–352.
J. of HRC & CC, 3, (1980), 147–148.
Chromatographia, vol. 8, (9), Sep. 1975, 449–451.
J. of Chrom., 167, (1978), 139–147.
Anal. Chem., vol. 51, (1979), 166–170.
Tsuje, Analytical Chem., vol. 51, (1), pp. 166–169, Jan. 1979.
Stan et al., Analytical Chem., vol. 50, No. 14, Dec. 1978, pp. 2161–2164.

*Primary Examiner*—Michael S. Marcus
*Attorney, Agent, or Firm*—Millard & Cox

[57] ABSTRACT

To avoid the problem of instrumental drift encountered when using an open-split interface between a temperature-programmed gas-liquid chromatography column and a mass spectrometer, the inert gas supplied to the open-split interface and the interface itself are heated to a temperature above the maximum temperature attained by the chromatography column during the analysis.

3 Claims, 2 Drawing Figures

METHOD AND APPARATUS FOR THE ANALYSIS OF MATERIALS BY CHROMATOGRAPHY AND MASS SPECTROMETRY

BACKGROUND OF THE INVENTION

The invention relates to a method and apparatus for the analysis of materials by chromatography and mass spectrometry. More specifically, the invention relates to a method and apparatus for overcoming certain problems which have been found to exist when a gas-liquid chromatography column operating at varying temperatures is coupled to a mass spectrometer by means of a so-called open-split interface.

The ability of gas-liquid chromatography to separate mixtures, especially complex mixtures of biological origin, is well known. It is also well known that by coupling the output of a gas-liquid chromatography column to the input of a mass spectrometer, one can obtain mass spectra of the various components eluted from the column, thereby greatly facilitating the identification of these components.

One problem encountered in using such a combination of gas-liquid chromatography and mass spectrometry for analytical purposes is that gas-liquid chromatography columns normally operate at about atmospheric pressure, whereas of course, the ionization chamber of a mass spectrometer must operate at very low pressure. To enable the chromatography column to be coupled to the mass spectrometer, a so-called open-split interface may be used. Such an open-split interface comprises an intake conduit which is connected to the outlet of the chromatography column and an outlet conduit for connection to the inlet of a mass spectrometer. The outlet conduit connected to the inlet of the mass spectrometer is made of small diameter (being typically a platinum or glass capillary tube of 0.1-0.2 mm. internal diameter) so that the interface can operate at about atmospheric pressure while the ionization chamber connected to the outlet conduit of the interface can operate at low pressures without excessive pumping requirements. The open ends of the intake and outlet conduits are separated by a gap and the material leaving the intake conduit jumps this gap surrounded by an atmosphere of inert gas, which is supplied to the interface by a gas inlet conduit which enters the interface adjacent the gap. The inert gas is usually helium. A sleeve having two open ends may be provided surrounding the open ends of the intake and outlet conduits; this sleeve, constitutes an adequate open slit.

Further details of known open-split interfaces are described in the following papers, the disclosures of which are herein incorporated by reference:

D. Henneberg, U. Henrichs and G. Schromburg, J. Chromatogr. 112, 343 (1975);

D. Henneberg, U. Henrichs and G. Schromburg, Chromatographia 8, 449 (1975);

D. Henneberg, U. Henrichs, H. Hurmann and G. Shcromburg, J. Chromatogr. 3, 147 (1980);

H. J. Stan and B. Abraham, Anal. Chem. 50, 2161 (1978); and

R. B. Hurley, J. High Res. Chromatogr. Chromatogr. Commun. 3, 147 (1980).

Open-split interfaces operate satisfactorily when the chromatography column is operating at a constant temperature. However, the resolution of very complex mixtures, usually of biological origin, can be greatly improved if the chromatography column is temperature-programmed, that is to say if the temperature at which the column operates is progressively increased during the course of each analysis from a lower temperature to an upper temperature. We have found that, if one attempts to use a temperature-programmed chromatography column with the open-split interfaces known hitherto, unreliable data can be obtained from the mass spectrometer because the base line signal of the total ionization monitor drifts so badly as to completely obscure the mass peaks or, at the least, sensitivity is sacrificed. Accordingly, there is a need for an open-split interface which can be used in conjunction with a temperature-programmed chromatography column and a mass spectrometer without causing severe drift in the total ionization monitor of the mass spectrometer. This invention provides such an open-split interface and a method for its use.

SUMMARY OF THE INVENTION

The invention provides a method for the analysis of a mixture by chromatographing the mixture on a gas-liquid chromatography column and passing the output from the column via an open-split interface into a mass spectrometer, wherein the temperature of the column is progressively increased during the analysis from a lower temperature to an upper temperature and an inert gas is supplied through the open-split interface. In the instant method, the inert gas is heated prior to its entry into the open-split interface to at least about the upper temperature reached by the column, the temperature of the inert gas being maintained substantially constant as the temperature of the column is progressively increased, and the open-split interface itself is also heated to at least about the upper temperature reached by the column.

The invention also provides apparatus for the analysis of materials by gas-liquid chromatography and mass spectroscopy, this apparatus comprising a gas-liquid chromatography column having an outlet, means for progressively increasing the temperature of the column from a lower temperature to an upper temperature, a mass spectrometer having an inlet, an open-split interface connecting the outlet of the column to the inlet of the mass spectrometer, means for supplying inert gas to the open-split interface and heating means for heating the inert gas and the open-split interface to above the upper temperature reached by the column.

Finally, the invention provides an open-split interface assembly, comprising an open-split interface and a gas inlet conduit for passing an inert gas to the interface. The open-split interface comprises an intake conduit for connection to the outlet of a gas-liquid chromatography column, this inlet having an open end and an outlet conduit for connection to the inlet of a mass spectrometer, this outlet conduit having an open end separated from the open end of the intake conduit by a gap. The assembly further comprises heating means for heating the gas inlet conduit and the open-split interface.

After careful analysis of the aforementioned problem of instrumental drift encountered when using an open-split interface with a temperature-programmed chromatography column, we have concluded that the major factor responsible for the instrumental drift is the varying temperature of the material entering the mass spectrometer. As the column heats up during the course of an analysis, the inert gas supplied to the interface also heats up, and since this inert gas constitutes the major portion of the material entering the mass spectrometer, the temperature of the material entering the mass spectrometer changes considerably during the course of analysis. Since the rate of flow of gas into the mass spectrometer is temperature-dependent (because the viscosity of gas increases with temperature) the change in temperature of gas entering the mass spectrometer causes a rapid change in the quantity of gas entering the mass spectrometer and the observed drift on the total ionization monitor thereof. Although we believe the foregoing analysis of the problem to be correct, we would emphasize that this analysis is in no way foreshadowed in the literature and that our invention is in no way restricted by our belief as to the source of the instrumental drift problem. By heating the inert gas before it reaches the gap in the open-split interface and by heating the interface itself, the material entering the mass spectrometer remains at a substantially constant temperature throughout the analysis and thus the drift problem is greatly reduced and, at least in some cases, the drift can be reduced to a point where it can be ignored in interpreting the mass spectroscopic results.

Although the heating of the inert gas and the interface may be achieved by using two separate heating means, one for heating the inert gas before it reaches the interface and a second one for heating the interface itself, it is more convenient to have a single heating means which performs both functions. Conveniently, the heating means has the form of heating block having walls defining an interface channel which accommodates the open-split interface and a gas channel which intersects the interface channel and through which gas can be passed into the interface channel. To ensure that the temperature of the inert gas reaching the interface remains truly constant, the inert gas is preferably supplied through a gas supply conduit passing through the gas channel to the open-split interface and having a helical portion disposed within the gas channel. In use, such a heating block will lie adjacent the oven of the mass spectrometer and will be exposed to heat from this oven. To prevent such heat affecting the results obtained from the instant apparatus, it is very desirable that the heating block be provided with an insulating jacket to shield it from the mass spectrometer oven.

As stated above, in the method and apparatus of the invention the inert gas must be heated above the upper temperature reached by the column during each analysis. It is preferred that the inert gas be heated above this upper temperature and preferably to a temperature of from about 10° to about 40° C. above this upper temperature prior to entry of the inert gas into the open-split interface. The optimum temperature for the inert gas appears to be about 25° C. above this upper temperature which is usually above 200° C. when analyzing biological materials, and frequently in the range of about 280° to about 320° C.

To ensure that the temperature of the inert gas entering the open-split interface does remain as constant as possible, it is desirable that the heating means used to heat this gas and the interface be provided with thermostatic control means.

DETAILED DESCRIPTION OF THE DRAWINGS

Figure 1:
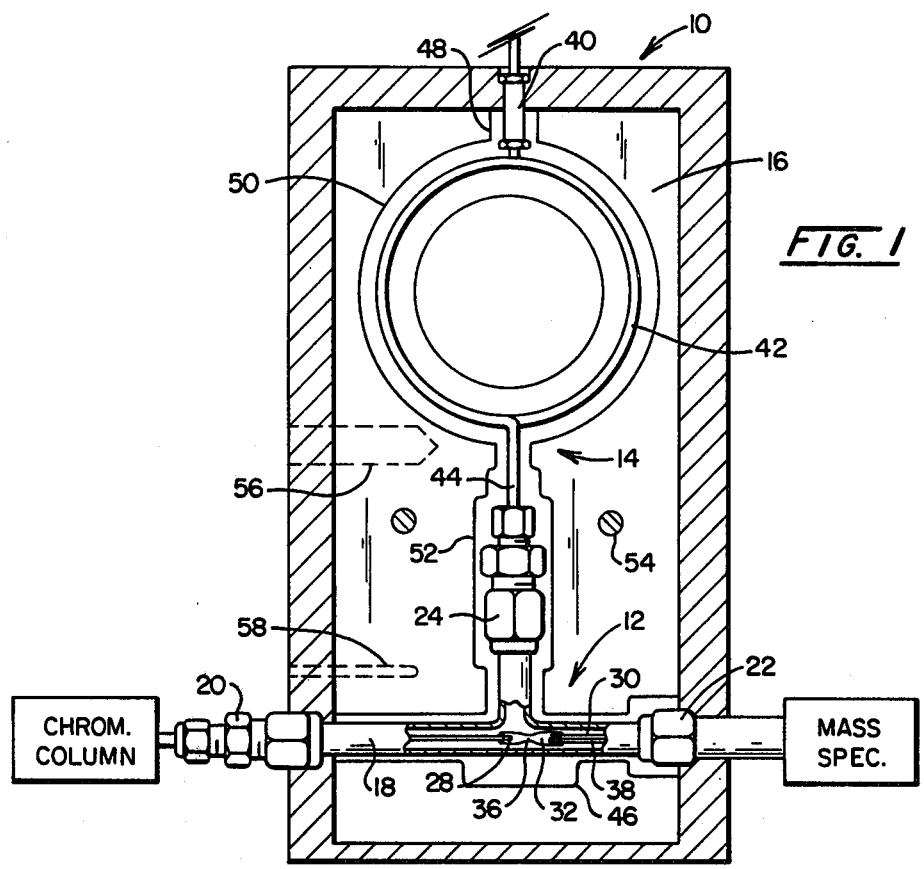
FIG. 1 is a top plan view of an open-split interface assembly of the invention with the top part of the heating block thereof removed and with the open-split interface shown in cross-section.

The open-split interface assembly (generally designated 10) shown in FIG. 1 comprises an open-split interface (generally designated 12), a gas inlet conduit (generally designated 14) and a heating block 16. The block 16 is provided with an insulating jacket 17 which shields the block 16 from the heat generated by the oven of a gas-liquid chromatography column lying adjacent thereto.

The open-split interface 12 itself comprises a glass T-piece 18 provided with adaptors 20, 22, and 24 at the extremities of its three arms. The output from a capillary gas-liquid chromatography column or packed columns (shown only schematically) enters the interface through a 1.6 mm. outside diameter glass capillary column 26, which is held in position by the adaptor 20. The tube 26 terminates at an open end 28 disposed within the central portion of the T-piece 18. The output from the interface passes via a platinum capillary tube 30 having an internal diameter of approximately 0.1 mm. (a glass capillary tube of similar diameter may alternatively be used) to the inlet oven of a mass spectrometer (shown only schematically). The tube 30 is axially aligned with the tube 26 and the open end 32 of the tube 30 is separated from the open end 28 of the tube 26 by a gap of 1.5–2.5 mm. An alignment jacket or sleeve 34, 15 mm. in length and open at both ends, surrounds the open ends 28 and 32. The sleeve 34 is constricted at its central portion 36. Disposed within the sleeve 34 adjacent the open end of the tube 32 is a blow-out line 38 through which an inert gas may be passed to prevent material giving rise to very intense gas chromatographic peaks (such as solvent or impurities) passing into the tube 30, thereby avoiding contamination of the ion source of the mass spectrometer with unwanted components while maintaining chromatographic resolution.

The gas inlet conduit 14 has three main sections, namely an inlet section 40 which is connected to a supply of helium gas, a helical section 42 comprising eight complete turns 25 mm. in diameter of 3.2 mm. outside diameter stainless steel tubing, and a third section 44 which is connected to the adaptor 24 on the T-piece 18. Note that the gas inlet conduit terminates at the adaptor 24, so that after passing through the gas inlet conduits 14 the gas flows down the side arm of the T-piece 18 to reach the main part of the T-piece. In use, helium gas is fed through the conduit 14 at about 10–12 ml./min.

The heating block 16 is formed in two parts, only the lower part being shown in FIG. 1. The complete heating block is an aluminum block 55×160×25 mm. and has milled therein an interface channel 46 which accommodates the main part of the T-piece 18 and a gas channel which accommodates the gas supply line 14 and the side arm of the T-piece 18. This gas channel comprises three sections, namely a first section 48 which accommodates the inlet section 40 of the gas supply line, a substantially toroidal section 50 which accommodates the helical part of the gas supply line and a third, substantially cylindrical section 52 which accommodates the section 44 of the gas supply line, the adaptor 24 and the side arm of the T-piece 18. The interface and gas channels are formed only in the lower half of the heating block 16, the upper part of the block being (apart from the recesses mentioned below) a simple cuboid.

The lower part of the heating block 16 is provided with two upstanding pins 54 which engage corresponding recesses in the upper part of the block, thereby maintaining the two halves of the block in the correct relative positions. The lower part of the heating block 16 also has a bore 56 which accommodates an electrical resistance heating element and a narrower bore 58 which receives a thermocouple. The thermocouple is connected to a thermostatic control unit (not shown) which controls the operation of the electrical resistance element in the bore 56 so as to keep the heating block 16 at a constant temperature.

To use the split interface assembly shown in FIG. 1, the upper part of the heating block 16 is placed in position on the pins 54, and the electrical resistance heating element and the thermocouple are placed within their respective bores and connected to the thermostatic control unit. The block is then allowed to heat up to its working temperature, which is preferably from 10° to 40° C. greater than the maximum temperature attained by the chromatography column during the analyses to be performed. The long gas purge line provided by the helical section 42 helps to ensure that the helium gas entering the T-piece 18 is at the correct temperature. Once the apparatus has been allowed to achieve thermal equilibrium, the first analysis may be begun in the chromatography column.

The apparatus shown in FIG. 1 was connected between a Varian 3700 gas chromatograph and an MAT-311A mass spectrometer. The chromatograph was temperature programmed from 40° C. to about 220° C. at 8° C./minute. When the heating means of the apparatus shown in FIG. 1 was switched off, the baseline drift of the total ionization monitor of the mass spectrometer was so severe that poor signal quality was derived therefrom. However, a similar run with the heating means switched on and maintained at 260° C. reduced the drift substantially to zero and thereby enabled the monitor to produce signals having substantially the same signal-to-noise ratio as that produced when the chromatograph was operated at a constant temperature. The sensitivity of the entire system when used with a temperature-programmed chromatograph was increased by at least two orders of magnitude.

Figure 2:
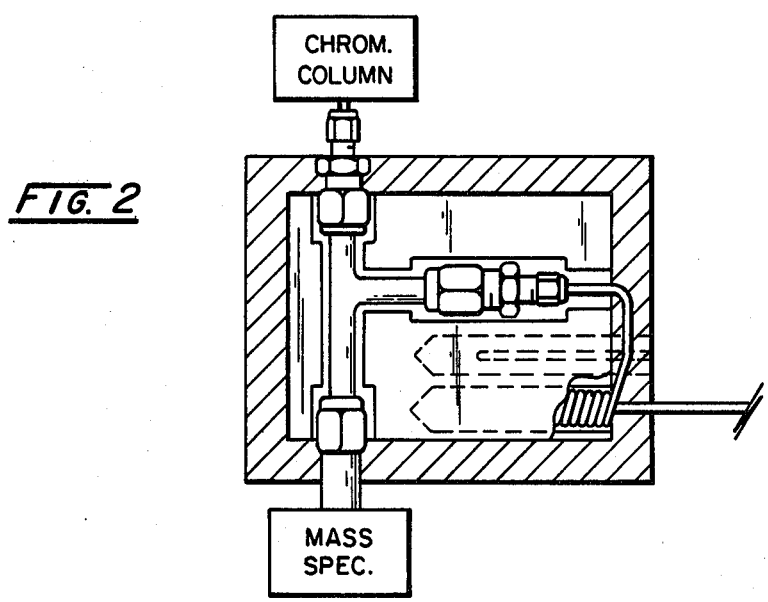
FIG. 2 is a top plan view of a second open-split interface assembly of the invention with parts of the heating block broken away to show the construction of the assembly.

The second open-split interface assembly of the invention shown in FIG. 2 is very similar to that shown in FIG. 1, but the heating block is of smaller dimensions in order to allow the interface to lie close to the wall of the oven surrounding the chromatography column. To reduce the size of the block, the relatively flat helical section 42 of the gas supply line 14 shown in FIG. 1, which has its axis perpendicular to the plane of the T-piece 18, is replaced by a much narrower helical section having more turns and having its axis parallel to the axis of the side arm of the T-piece. The electrical resistance heating element and thermocouple are placed within two separate bores lying between the helical section of the gas supply line and the side arm of the T-piece these two bores being shown superimposed in FIG. 2.

It has been found that the preferred embodiments of the invention described above, when operated at the optimum temperature, which is about 25° C. greater than the maximum temperature of the chromatography column during each analysis, reduce the drift of the total ionization monitor of the mass spectrometer by a factor of at least 100 and in some cases as much as 1,000, thereby enabling the mass spectrometer to produce mass spetra without any significant drift.

It will be apparent to those skilled in the art that numerous modifications and variations may be made in the preferred embodiments of the invention described above. Accordingly, the foregoing description is to be construed in an illustrative and not in a limitative sense, the scope of the invention being defined solely by the appended claims.

We claim:

1. An apparatus for the analysis of materials by temperature-programmed gas chromatography and mass spectrometry, said apparatus comprising:
   a gas chromatography column having an outlet;
   first heating means for progressively increasing the temperature of said column from a lower temperature to an upper temperature;
   a mass spectrometer having an inlet;
   an open-split interface connecting said outlet of said column to said inlet of said mass spectrometer and;
   means of supplying inert gas to said open-interface, the improvement which comprises second heating means for heating said inert gas and said interface to above said upper temperature, thereby reducing the instrumental drift of the base line signal of the total ionization of said mass spectrometer, said second heating means comprising a heating block having walls defining an interface channel which accomodates said interface and a gas channel which intersects said interface channel and through which gas can be passed into said interface channel, said heating block being provided with thermostatic control means for maintaining the temperature of said block substantially constant during said progressive increase of temperature of said column, and wherein said means for supplying said inert gas to said open-split interface comprises a gas supply line having its one end connected to said open-split interface, said gas supply line having a helical section disposed within said gas channel, said helical section increasing the residence time of said gas within said gas channel and thereby improving the uniformity of temperature of said gas reaching said open-split interface.

2. Apparatus according to claim 1 wherein said gas channel has a substantially toroidal section which accomodates said helical part of said gas supply line.

3. Apparatus according to claim 1 wherein a portion of said gas channel is substantially cylindrical in form and said helical section of said gas supply line is disposed within said cylindrical section of said gas channel.

* * * * *